(12) United States Patent
Baltz et al.

(10) Patent No.: US 10,440,952 B2
(45) Date of Patent: Oct. 15, 2019

(54) USE OF ACTIVE SUBSTANCES FOR CONTROLLING VIRUS INFECTION IN PLANTS

(71) Applicant: Bayer CropScience Aktiengesellschaft, Monheim am Rhein (DE)

(72) Inventors: Rachel Baltz, Collonges au Mont d'Or (FR); David Bernier, Lyons (FR); Florence Jay-Brioudes, Zürich (CH); Thomas Knobloch, Alix (FR); Maxime Vitel, Fontaines sur Saône (FR); Olivier Voinnet, Zürich (CH)

(73) Assignee: Bayer Corp Science Aktiengesellschaft, Monheim am Rhein (DE)

( * ) Notice: Subject to any disclaimer, the term of this patent is extended or adjusted under 35 U.S.C. 154(b) by 0 days.

(21) Appl. No.: 16/069,242

(22) PCT Filed: Jan. 12, 2017

(86) PCT No.: PCT/EP2017/050584
§ 371 (c)(1),
(2) Date: Jul. 11, 2018

(87) PCT Pub. No.: WO2017/121810
PCT Pub. Date: Jul. 20, 2017

(65) Prior Publication Data
US 2019/0021327 A1    Jan. 24, 2019

(30) Foreign Application Priority Data
Jan. 13, 2016  (EP) .................... 16290009

(51) Int. Cl.
| *A01N 43/80* | (2006.01) |
| *A01G 7/06* | (2006.01) |
| *C07D 261/12* | (2006.01) |
| *C07D 409/06* | (2006.01) |
| *A01G 22/60* | (2018.01) |
| *A01G 22/50* | (2018.01) |
| *A01G 22/05* | (2018.01) |
| *A01G 17/02* | (2006.01) |
| *A01G 23/00* | (2006.01) |

(52) U.S. Cl.
CPC ............ *A01N 43/80* (2013.01); *A01G 7/06* (2013.01); *C07D 261/12* (2013.01); *C07D 409/06* (2013.01); *A01G 17/02* (2013.01); *A01G 22/05* (2018.02); *A01G 22/50* (2018.02); *A01G 22/60* (2018.02); *A01G 23/00* (2013.01)

(58) Field of Classification Search
None
See application file for complete search history.

(56) References Cited

U.S. PATENT DOCUMENTS

| 8,853,172 | B2 | 10/2014 | Masuta et al. |
| 2003/0139432 | A1 | 7/2003 | Kohle et al. |
| 2004/0186149 | A1 | 9/2004 | Kohle et al. |
| 2009/0233916 | A1 | 9/2009 | Kohle et al. |
| 2012/0172580 | A1 | 7/2012 | Masuta et al. |
| 2015/0250169 | A1 | 9/2015 | Ihori et al. |

FOREIGN PATENT DOCUMENTS

| EP | 2 902 387 A1 | 8/2015 |
| WO | 01/82701 A1 | 11/2001 |
| WO | 2007/104669 A2 | 9/2007 |
| WO | 2011/030816 A1 | 3/2011 |
| WO | 2012/016048 A1 | 2/2012 |
| WO | 2013011010 A1 | 1/2013 |
| WO | 2014/050894 A1 | 4/2014 |

OTHER PUBLICATIONS

Herms, et al., "A Strobilurin Fungicide Enhances the Resistance of Tobacco against Tobacco Mosaic Virus and Pseudomonas syringae pv tabaci," Plant Physiology, (2002), vol. 130: 120-127.
Shimura, et al., "Viral induction and suppression of RNA silencing in plants," Biochimica et Biophysica Acta, (2011), vol. 1809: 601-612.
Pumplin, et al., "RNA silencing suppression by plant pathogens: defence, counter-defence and counter-counter-defence," Nature Reviews Microbiology, (2013), vol. 11: 745-60.
PCT International Search Report for PCT/EP2017/050584, dated Mar. 21, 2017.

*Primary Examiner* — Kamal A Saeed
(74) *Attorney, Agent, or Firm* — McBee Moore Woodward & Vanik IP, LLC

(57) ABSTRACT

The present invention relates to the use of specific active substances, alone or in combination, for controlling virus infections in plants and to a method for using said specific active substances for controlling said virus infections in the field of plant protection and the protection of materials.

14 Claims, 2 Drawing Sheets

Figure 3

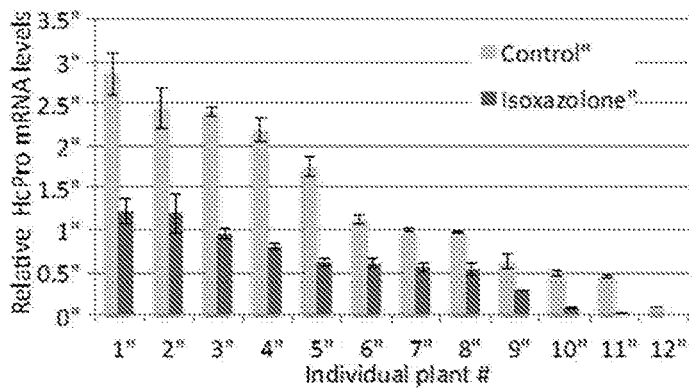

Figure 4

| ID | Isomer | R1 | R2 | Average % chlorosis |
|---|---|---|---|---|
| 1 | 4Z | 4-bromo-5-ethyl-2-thienyl | 2-chlorophenyl | 67.9 |
| 2 | 4Z | 3-(methylsulfanyl)-2-thienyl | 2-chlorophenyl | 62.0 |
| 3 | 4Z | 4-bromo-5-[(methylsulfanyl)methyl]-2-thienyl | 2-chlorophenyl | 59.7 |
| 4 | 4Z | 2-Thienyl | 2-chlorophenyl | 57.0 |
| 5 | 4Z | 3-(methoxymethyl)-2-thienyl | 2-chlorophenyl | 57.0 |
| 6 | 4Z | 2-Thienyl | 3-chlorophenyl | 52.9 |
| 7 | 4Z | 2-Thienyl | 2-methoxyphenyl | 50.9 |
| 8 | 4Z | 2-Thienyl | 2-Fluorophenyl | 50.9 |
| 9 | 4E | 5-methyl-2-thienyl | 2-chlorophenyl | 49.9 |
| 10 | 4Z | 2-Thienyl | 4-methylphenyl | 48.0 |
| 11 | 4Z | 2-Thienyl | Phenyl | 46.8 |
| 12 | 4Z | 2-Thienyl | 4-Fluorophenyl | 44.6 |
| 13 | 4E | 4-methylphenyl | 2-chlorophenyl | 44.5 |
| 14 | 4E | 2-Thienyl | 4-methoxyphenyl | 44.3 |
| 15 | 4E | 2-Thienyl | Phenyl | 43.7 |
| 16 | 4Z | 2-methylphenyl | 2-chlorophenyl | 43.5 |
| 17 | 4Z | 5-bromo-2-thienyl | Phenyl | 43.0 |
| 18 | 4Z | 2-Thienyl | 2,4-dichlorophenyl | 42.7 |
| 19 | 4Z | 2-Thienyl | 2,3-dichlorophenyl | 42.5 |
| 20 | 4Z | 5-phenyl-2-thienyl | 2-chlorophenyl | 42.0 |
| 21 | 4Z | 4-bromo-5-methyl-2-thienyl | 2-chlorophenyl | 41.8 |
| 22 | 4Z | 5-chloro-2-thienyl | 2-chlorophenyl | 40.8 |
| 23 | 4E | 2-Thienyl | 3-methoxyphenyl | 38.6 |
| 25 | 4E | 5-methyl-2-thienyl | Phenyl | 38.2 |
| 26 | 4Z | 2-Thienyl | 2,5-dichlorophenyl | 37.9 |
| 27 | 4Z | 3-methyl-2-thienyl | 2-chlorophenyl | 37.9 |
| 28 | 4Z | 2-Thienyl | 4-methoxyphenyl | 36.6 |
| 29 | 4Z | 4-phenyl-2-thienyl | 2-chlorophenyl | 35.8 |
| 30 | 4Z | Ph | 2-chlorophenyl | 35.6 |
| 31 | 4Z | 2-Thienyl | 2-chloro-5-fluorophenyl | 34.8 |
| 32 | 4Z | 5-methyl-2-thienyl | 4-methoxyphenyl | 34.4 |
| 33 | 4Z | 2-Thienyl | 2-methylphenyl | 32.9 |
| 34 | 4E | 2,6-dichlorophenyl | 2-chlorophenyl | 32.7 |
| 35 | 4E | 2,4,6-trimethylphenyl | 2-chlorophenyl | 32.5 |
| 36 | 4E | 2,6-dimethylphenyl | 2-chlorophenyl | 29.4 |
| 37 | 4Z | 2-Thienyl | 3,4-dichlorophenyl | 29.1 |
| 38 | 4Z | 4-bromo-2-thienyl | Phenyl | 27.5 |
| 39 | 4Z | 3-methyl-2-thienyl | 4-methylphenyl | 27.5 |
| 40 | 4Z | 2,4,5-trimethylphenyl | 2-chlorophenyl | 26.4 |
| 41 | 4Z | 5-methyl-2-thienyl | 2-chlorophenyl | 26.1 |

_US 10,440,952 B2_

USE OF ACTIVE SUBSTANCES FOR CONTROLLING VIRUS INFECTION IN PLANTS

CROSS-REFERENCE TO RELATED APPLICATIONS

This application is a National Stage entry of International Application No. PCT/EP2017/050584, filed Jan. 12, 2017, which claims priority to European Patent Application No. 16290009.6, filed Jan. 13, 2016.

FIELD

The present invention relates to the use of active substances for stimulating the natural defense mechanism of plants against viruses in order to control virus infections in plants and to methods for controlling virus infections in plants. The present invention also pertains to the use of active substances for activating the RNA-interference-based natural defense mechanism (also designated herein as RNA-silencing-based natural defense mechanism) of plants against viruses.

DESCRIPTION OF RELATED ART

Plant viruses are responsible for major crop damages around the world. Indeed, some virus families, such as the Potyviridae, cause critical yield losses both in developed and emerging countries, conflicting with the ever-increasing food demand. To limit virus infections and spread, disease management is mainly conducted via prevention, as curative treatments are not or poorly efficient.

Several compounds have been identified for trying to control plant viruses.

WO2011/030816 teaches the use of certain ascorbic acid derivatives to control certain plan viruses.

WO2012/016048 provides for the use of azide-modified biomolecules as antiviral agents, including against plant viruses.

WO2014/050894 teaches the use of other ascorbic acid related compounds to control plant viruses.

Plants have evolved to continuously cope with threats using their available resources and balancing them between growth or defense against biotic and abiotic threats. RNA silencing plays a major part in this balance by dynamically linking developmental programs and environmental stress responses to gene expression changes through transcriptional gene silencing (TGS) and post-transcriptional gene silencing (PTGS). Disease resistance in plants relies on preformed barriers, toxic secondary metabolites and inducible defense mechanisms. Upon pathogen recognition, plants often initiate hypersensitive response, leading to cell death at the infection site and preventing the pathogen from spreading. In addition, pathogen detection triggers various inducible systemic defenses, in parts of the plant distant from the primary infection site. This process, known as Systemic Acquired Resistance (SAR), is effective in many plant species. The resistance achieved is long-lasting and effective against subsequent infections by a broad range of pathogens e.g. fungi, bacteria and viruses.

The Strobilurin class of fungicides comprises a variety of synthetic plant-protecting compounds with broad-spectrum. In 2002, the strobilurin Pyraclostrobin has been demonstrated to enhance the resistance of tobacco against infection by either tobacco mosaic virus (TMV) or the wildfire pathogen _Pseudomonas syringae pv tabaci_ (Herms et al., Plant Physiology 2002, 130: 120-127). Pyraclostrobin was also able to enhance TMV resistance in NahG transgenic tobacco plants unable to accumulate significant amounts of the endogenous salicylic acid. Pyraclostrobin enhances TMV resistance in tobacco either by acting downstream of Salicylic Acid (SA) in the SA signaling mechanism or by functioning independently of SA. The latter assumption is the more likely because, in infiltrated leaves, Pyraclostrobin did not cause the accumulation of SA-inducible pathogenesis-related (PR)-1 proteins that often are used as conventional molecular markers for SA-induced disease resistance. Application of strobilurins is described either alone (WO 01/82701) or in mixture with metiram (WO 2007/104669).

Among the plant defense responses to phytoviruses, the antiviral RNA silencing pathway is the broadest defense system affecting both the local and the systemic accumulation of a wide range of viruses. RNA silencing is a mechanism that directly defends plant host cells against exogenous nucleic acids, including viruses and transposable elements. This defense is triggered by double-stranded RNA (dsRNA), derived from amplification of invasive nucleic acids, which is processed by the host into small interfering RNAs (siRNAs) that are 20-24 nucleotides (nt) in size. These siRNAs are then used to guide the silencing of the viral or transposable element RNA or DNA through PTGS or TGS, respectively.

RNA silencing is then a potent antiviral mechanism whereby small interfering siRNAs processed by the enzyme Dicer from viral double-stranded RNA replication intermediates are loaded into ARGONAUTE effector proteins and turned back onto the invader's RNA genome to induce its degradation. This innate immune response is remarkably versatile because, being solely programmed by structural and nucleotide-sequence genomic features, it can respond to virtually any plant virus (Shimura et al., 2011, _Biochimica et Biophysica Acta_ 1809: 601-612).

Attesting the importance of RNA silencing in plant defense, plants impaired in siRNA production or activity are hyper-susceptible to phytoviruses, and conversely many viruses have evolved suppressors of RNAi in order to maintain virulence (Voinnet O. et al, Nature Review Microbiology 2013 November; 11(11):745-60).

In conclusion, although certain compounds have been identified in the past as potential inducers of certain plant defense mechanisms against viruses, there remains a need to provide active substances suitable for stimulating the natural defense mechanism of plants against viruses, in particular for stimulating the broad non-specific RNA-silencing-based defense mechanism of plants against viruses in order to control viral diseases in plants.

DEFINITIONS

The term "$(C_1-C_6)$alkyl" as used herein refers to a branched- or straight-chain alkyl group containing from 1 to 6 carbon atoms. Representative examples of $(C_1-C_6)$alkyl include methyl, ethyl, n-propyl, i-propyl and the different butyl, pentyl or hexyl isomers.

The term "halogen" as used herein refers to a fluorine, chlorine, iodine or bromine atom.

The term "$(C_1-C_6)$alkoxy" as used herein refers to the radical —O-$(C_1-C_6)$alkyl wherein the term "$(C_1-C_6)$alkyl" is as defined above. Representative examples of $(C_1-C_6)$ alkoxy include methoxy, ethoxy, n-propyloxy, isopropyloxy, and the different butyloxy, pentyloxy or hexyloxy isomers.

The term "$(C_1-C_6)$alkylthio" as used herein refers to the radical —S-$(C_1-C_6)$alkyl wherein the term "$(C_1-C_6)$alkyl" is as defined above. Representative examples of $(C_1-C_6)$alkylthio include methylthio, ethylthio, propylthio and butylthio. "$(C_1-C_6)$alkylthio" is also referred herein as "$(C_1-C_6)$alkylsulfanyl" (e.g. methylsulfanyl refers to the radical Me-S-).

The term "$(C_1-C_6)$alkoxy$(C_1-C_6)$alkyl" as used herein refers to the radical —$(C_1-C_6)$alkyl-O-$(C_1-C_6)$alkyl wherein the terms "$(C_1-C_6)$alkyl" are as defined above.

The term "$(C_1-C_6)$alkylthio$(C_1-C_6)$alkyl" as used herein refers to the radical —$(C_1-C_6)$alkyl-S-$(C_1-C_6)$alkyl wherein the terms "$(C_1-C_6)$alkyl" are as defined above. "$(C_1-C_6)$alkylthio$(C_1-C_6)$alkyl" is also referred herein as "$(C_1-C_6)$alkylsulfanyl$(C_1-C_6)$alkyl" (e.g. methylsulfanylmethyl refers to the radical Me-S-$CH_2$-).

The expression "may be substituted" as used herein (e.g. a phenyl that may be substituted), means that the substitution is optional and therefore includes both unsubstituted and substituted atoms or groups (e.g. unsubstituted and substituted phenyl). When an atom or group is substituted, any hydrogen on the designated atom or group can be replaced with a substituent (up to and including that every hydrogen is replaced with a substituent) provided that the normal valency of the designated atom or group is not exceeded and that the substitution results in a stable compound. The term "active substance" as used herein designates a compound of formula (I) as described herein or any mixtures thereof.

SUMMARY

It has now been found that compounds of formula (I) as disclosed herein are suitable for stimulating the natural defense mechanism of plants against viruses, in particular for stimulating the RNA-silencing-based defense mechanism of plants against viruses. Therefore, the compounds of formula (I) as disclosed herein may be useful for controlling viral diseases in plants. The term "control" or "controlling" as used herein designates a preventive or curative control.

Accordingly, the present invention relates to a method for controlling viral diseases in plants, more specifically to a method for stimulating the natural defense mechanism of plants against viruses, in particular for stimulating the RNA-silencing-based defense mechanism of plants against viruses. The method comprises applying to the plants one or more compounds of formula (I):

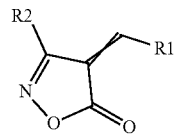

(I)

wherein

R1 is a thienyl (preferably a thien-2-yl) or phenyl, wherein said thienyl or phenyl may be substituted with one or more substituents independently selected from the group consisting of halogen, $(C_1-C_6)$alkyl, $(C_1-C_6)$alkylthio, $((C_1-C_6)$alkoxy$)(C_1-C_6)$alkyl, $((C_1-C_6)$alkylthio$)(C_1-C_6)$alkyl and phenyl; and R2 is a phenyl which may be substituted with one or more substituents independently selected from the group consisting of halogen, $(C_1-C_6)$alkyl and $(C_1-C_6)$alkoxy.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 illustrates the RT-qPCR analyses on HcPro mRNA accumulation in systemic tissues at six days post-infection. Error bars represent standard deviation from three independent PCR results.

FIG. 4 sets forth the results of evaluating Isoxazolone (compound ID No. 4) and analogs thereof on SUC-SUL reporter plants. The level of chlorosis of mock treated plant reached 10%.

DETAILED DESCRIPTION OF A PREFERRED EMBODIMENT

Figure 1:
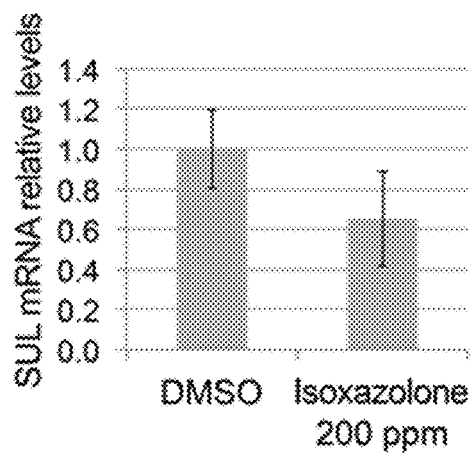
FIG. 1 illustrates the qPCR analysis of the SUL mRNA relative levels in SUC-SUL plants seven days after treatment with DMSO only or Isoxazolone, normalized to EXP10. Error bars represent standard deviation from three independent experiments.

In some embodiments, the active substance is a compound of formula (I) wherein:
R1 is a thienyl (preferably a thien-2-yl) or phenyl, wherein said thienyl or phenyl may be substituted with one, two or three substituents independently selected from the group consisting of bromine, chlorine, methyl, ethyl, methylthio, (methylthio)methyl, phenyl and methoxymethyl; and/or
R2 is a phenyl which may be substituted with one or two substituents independently selected from the group consisting of chlorine, fluorine, methyl and methoxy.

In some preferred embodiments, the active substance is a compound of formula (I) wherein:
R1 is selected from the group consisting of 2-thienyl, phenyl, 3-methyl-2-thienyl, 5-methyl-2-thienyl, 2-methylphenyl, 4-methylphenyl, 4-phenyl-2-thienyl, 5-phenyl-2-thienyl, 4-bromo-2-thienyl, 5-bromo-2-thienyl, 5-chloro-2-thienyl, 4-bromo-5-methyl-2-thienyl, 4-bromo-5-ethyl-2-thienyl, 3-(methylsulfanyl)-2-thienyl, 4-bromo-5-[(methylsulfanyl)methyl]-2-thienyl, 3-(methoxymethyl)-2-thienyl, 2,6-dimethylphenyl, 2,4,5-trimethylphenyl, 2,4,6-trimethylphenyl and 2,6-dichlorophenyl; and/or
R2 is selected from the group consisting of phenyl, 2-chlorophenyl, 2-fluorophenyl, 3-chlorophenyl, 4-fluorophenyl, 2,3-dichlorophenyl, 2,4-dichlorophenyl, 2,5-dichlorophenyl, 3,4-dichlorophenyl, 2-chloro-5-fluorophenyl, 2-methylphenyl, 4-methylphenyl, 2-methoxyphenyl, 3-methoxyphenyl and 4-methoxyphenyl.

In some embodiments, the active substance is a compound of formula (I) wherein wherein R1 and R2 are selected such as to provide the specific compounds disclosed in FIG. 4.

Compounds of formula (I) may be suitably prepared as disclosed in WO2011/161035 (Bayer CropScience AG).

An effective amount of active substance is typically applied to the plants. The effective amount of active substance which is applied to the plants will depend on various factors, such as the nature of the active substance, the formulation, the plants being targeted (plants nature and plants part), the application method, the purpose of the treatment (prophylactic or therapeutic) and the virus being targeted. The amount applied to the plants may suitably range from 0.01 to 5 kg/ha, or from 0.1 to 3 kg/ha, or from 0.5 to 2 kg/ha.

As indicated above, the active substance is applied to the plants. The term "plants" as used herein include plants and parts thereof, such as the aerial and/or subterranean parts of the plants as well as the harvested material. Subterranean plants parts include root, rhizomes, tubers, suckers, slips, seeds and seed. The aerial plant parts include stem, bark, shoot, leaf, flower, fruits, fruiting bodies, stalk, needles and branches. Thus, the active substance may be efficiently applied to the root, rhizomes, tubers, suckers, slips, seeds, seed, stem, bark, shoot, leaf, flower, fruits, fruiting bodies, stalk, needles, branches, harvested material of the plants. In alternative embodiments, the method for controlling viral diseases in plants comprises applying the disclosed active substance to the plants' habitat and/or store.

The active substance can be efficiently applied to a large variety of plants. It may be applied to plants of the varieties which are commercially available or in use. However, plant varieties are also understood as meaning plants with novel traits which have been bred either by traditional breeding, by mutagenesis or with the aid of recombinant DNA techniques and/or to plants which can be obtained by traditional breeding and optimization methods or else by biotechnological and genetic engineering methods or by combinations of these methods; this includes the transgenic plants and the plants which are capable or not of being protected by Plant Breeders' Rights.

The active substance may also be efficiently applied to genetically modified organisms (GMOs). Genetically modified plants are plants in which a heterologous gene has been stably integrated into the genome. The expression "heterologous gene" essentially means a gene which has been provided or assembled outside the plants and, when introduced into the nuclear, chloroplastic or mitochondrial genome, imparts novel or improved agronomic or other properties to the transformed plant by expressing a protein or polypeptide of interest or by down regulating or silencing another gene which is present in the plant, or other genes which are present in the plant (using, for example, antisense technology, cosuppression technology or RNAi technology [RNA interference]). A heterologous gene that is located in the genome is also called a transgene. A transgene that is defined by its particular location in the plant genome is referred to as a transformation event, or transgenic event.

All plants which have genetic material which imparts, to these plants, especially advantageous, useful traits (whether obtained by breeding and/or by biotechnology) may be treated by the disclosed method.

Plants and plant varieties which can likewise be treated in accordance with the invention are those plants which are resistant to one or more abiotic stress factors. Abiotic stress conditions can include, for example, drought, chill and heat conditions, osmotic stress, water-logging, elevated soil salt content, elevated exposure to minerals, ozone conditions, high-light conditions, limited availability of nitrogen nutrients, limited availability of phosphorus nutrients or the avoidance of shade.

Plants and plant varieties which can likewise be treated in accordance with the invention are those plants which are characterized by enhanced yield characteristics. Enhanced yield in these palm plants can be the result of, for example, improved plant physiology, improved plant growth and improved plant development, such as water utilization efficiency, water retention efficiency, improved nitrogen utilization, improved carbon assimilation, improved photosynthesis, increased germination efficiency and modified maturation. The yield can furthermore be influenced by improved plant architecture (under stress conditions and under nonstress conditions), among which early flowering, flowering control for the production of hybrid seed, seedling vigour, plant size, internode number and distance, root growth, seed size, fruit size, pod size, pod or ear number, number of seeds per pod or ear, seed mass, enhanced seed filling, reduced seed dispersal, reduced pod dehiscence, and lodging resistance. Further yield traits include seed composition, such as carbohydrate content, protein content, oil content and oil composition, nutritional value, reduction in antinutritional compounds, improved processability and improved storability.

Plants which can likewise be treated in accordance with the invention are hybrid plants that already express the characteristics of heterosis, or hybrid vigour, which generally results in higher yield, higher vigour, better health and better resistance to biotic and abiotic stress factors. Such plants are typically generated by crossing an inbred male-sterile parent line (the female parent) with another inbred male-fertile parent line (the male parent). The hybrid seed is typically harvested from the male-sterile plants and sold to growers. Male-sterile plants can sometimes (for example in maize) be generated by detasseling (i.e. the mechanical removal of the male reproductive organs or the male flowers); however, more typically, male sterility is the result of genetic determinants in the plant genome. In this case, in particular when seed is the desired product which is to be harvested from the hybrid plants, it is typically useful to ensure that male fertility in hybrid plants which contain the genetic determinants responsible for male sterility is fully restored. This can be achieved by ensuring that the male parents have appropriate fertility restorer genes which are capable of restoring male fertility in hybrid plants which contain the genetic determinants responsible for male sterility. Genetic determinants for male sterility can be located in the cytoplasm. Examples of cytoplasmic male sterility (CMS) have been described for example for Brassica species (WO 1992/005251, WO 1995/009910, WO 1998/27806, WO 2005/002324, WO 2006/021972 and U.S. Pat. No. 6,229,072). However, genetic determinants for male sterility may also be located in the nuclear genome. Male-sterile plants can also be obtained by plant biotechnology methods, such as genetic engineering. A particularly advantageous means for generating male-sterile plants is described in WO 89/10396, in which, for example, a ribonuclease such as a barnase is selectively expressed in the tapetum cells in the stamens. The fertility can then be restored by expression in the tapetum cells of a ribonuclease inhibitor such as barstar (for example WO 1991/002069).

The active substance is particularly suitable for controlling viral diseases in the following plants: cotton, flax, grapevine, fruit, vegetables, such as *Rosaceae* sp. (for example pome fruits such as apples and pears, but also stone fruits such as apricots, cherries, almonds and peaches, and soft fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for example banana trees and plantations), *Rubiaceae* sp. (for example coffee), *Theaceae* sp., *Sterculiceae* sp., *Rutaceae* sp. (for example lemons, oranges and grapefruit); *Solanaceae* sp. (for example tomatoes), *Liliaceae* sp., *Asteraceae* sp. (for example lettuce), *Umbelliferae* sp., *Cruciferae* sp., *Chenopodiaceae* sp., *Cucurbitaceae* sp. (for example cucumber), *Alliaceae* sp. (for example leek, onion), *Papilionaceae* sp. (for example peas); major crop plants, such as *Gramineae* sp. (for example maize, turf, cereals such as wheat, rye, rice, barley, oats, millet and triticale), *Asteraceae* sp. (for example sunflower), *Brassicaceae* sp. (for example white cabbage, red cabbage, broccoli, cauliflower, Brussels sprouts, pak Choi, kohlrabi, radishes, and oilseed rape, mustard, horseradish and cress), *Fabacae* sp. (for example bean, peanuts), *Papilionaceae* sp. (for example soya bean), *Solanaceae* sp. (for example potatoes), *Chenopodiaceae* sp. (for example sugar beet, fodder beet, swiss chard, beetroot); useful plants and ornamental plants for gardens and wooded areas; and genetically modified varieties of each of these plants.

More specifically, the active substance is suitable for controlling viral diseases in vegetables.

The active substance is particularly suitable for controlling viruses of the following families or genus: *Caulimoviridae, Geminiviridae, Bromoviridae, Closteroviridae, Cornoviridae Potyviridae, Sequiviridae, Tombusviridae, Rhabdoviridae, Bunyaviridae, Partitiviridae, Rheoviridae, Capillovirus, Carlavirus, Enamovirus, Furovirus, Hordeivirus, Idaeovirus, Luteovirus, Marafivirus, Potexvirus, Sobemovirus, Tenuivirus, Tobamovirus, Tobravirus, Trichovirus, Tymovirus* and *Umbravirus*.

Preferably, the active substance is used for controlling viruses of the following species: Turnip mosaic virus, turnip crinkle virus, bean pod mottle virus, cauliflower mosaic virus, tobacco mosaic virus, tomato bushy stunt virus, rice ragged stunt virus, cucumber mosaic virus, barley yellow dwarf virus, beet yellows virus, lettuce yellows virus, maise mosaic virus, peanut stunt virus and potato virus Y.

The active substance can be applied to the plants in any suitable forms. For example, the active substance may be applied in the form of a suspension, e.g. water- or oil-based suspension, emulsion, solution, powder such as wettable powder, foam, paste, granules, microparticles, aerosols or microencapsulations. Suitable formulations can be prepared in conventional manners. The formulations comprising the active substance may be ready-for-use compositions, i.e. compositions that can be directly applied to the plants by a suitable device, or they may be in the form of commercial concentrates which have to be diluted prior to use.

The formulations may comprise the active substance alone or in combination with other active substances such as insecticides, attractants, sterilants, bactericides, acaricides, nematicides, further fungicides, growth-regulating substances, herbicides, safeners and/or fertilizers.

The active substance or formulations comprising thereof may be applied to the plants in any customary manners, e.g. watering, spraying, dusting, atomizing. The active substance may be directly or indirectly applied to the plants, the environment, the habitat and/or the store. For example, the active substance can be injected into or below the bark, poured or sprayed around the plant onto the ground (soil, sandy soil, gravelly soil, rocky soil, loamy soil or mixed soil). A further type of application is the spraying onto the plant and its plant parts. In dry form, the active substance composition can be admixed to the ground material (soil, sandy soil, gravelly soil, rocky soil, loamy soil or mixed soil) and/or to the seeds. The active substance can be applied to the irrigation system, either in dry or else in liquid form. The active substance is preferably applied to the plants by spraying.

The present invention also relates to the use of compounds of formula (I) as disclosed herein for controlling viral diseases in plants, more specifically for stimulating the natural defense mechanism of plants against viruses, in particular for stimulating the RNA-silencing-based defense mechanism of plants against viruses. The plants and/or viruses are as disclosed above.

The compounds of formula (I) stimulate the RNA-silencing-based defense mechanism of the plants through an increase in small RNA production. Advantageously, the ability of the compounds of formula (I) to increase small RNA production can also be used in genetically modified plants transformed with an RNAi construct designed to improve agronomic traits and/or to provide resistance against pathogens (e.g. bacteria, fungi), resistance against insect/pest and/or stress tolerance. Therefore, the present invention also relates to the use of one or more compounds of formula (I) to improve agronomic traits and/or to provide resistance against pathogens, resistance against insect/pest and/or stress tolerance in genetically modified plants transformed with an RNAi construct through enhancement of small RNA production.

The present invention also relates to a compound of formula (I) and/or a composition comprising thereof, wherein the compound of formula (I) is as follows:

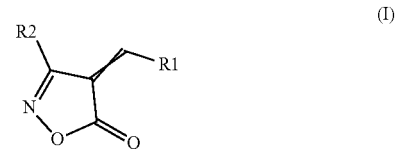

Wherein:
R1 is selected from the group consisting of 2-methylphenyl, 4-methylphenyl, 2,6-dimethylphenyl, 2,4,5-trimethylphenyl, 2,4,6-trimethylphenyl and 2,6-dichlorophenyl; and
R2 is 2-chlorophenyl.

The composition of the present invention typically comprises, in addition to the compound of formula (I), one or more acceptable carriers, in particular one or more agriculturally acceptable carriers.

A carrier is a natural or synthetic, organic or inorganic substance with which the active ingredients are mixed or combined for better applicability, in particular for better application to plants, plant parts or seeds. The carrier, which may be solid or liquid, is generally inert.

Examples of suitable solid carriers include, but are not limited to, ammonium salts, natural rock flours, such as kaolins, clays, talc, chalk, quartz, attapulgite, montmorillonite or diatomaceous earth, and synthetic rock flours, such as finely divided silica, alumina and silicates. Examples of typically useful solid carriers for preparing granules include, but are not limited to, crushed and fractionated natural rocks such as calcite, marble, pumice, sepiolite and dolomite, synthetic granules of inorganic and organic flours and granules of organic material such as paper, sawdust, coconut shells, maize cobs and tobacco stalks.

Examples of suitable liquid carriers include, but are not limited to, water, polar and nonpolar organic chemical liquids, for example from the classes of aromatic and nonaromatic hydrocarbons (such as cyclohexane, paraffins, alkylbenzenes, xylene, toluene alkylnaphthalenes, chlorinated aromatics or chlorinated aliphatic hydrocarbons such as chlorobenzenes, chloroethylenes or methylene chloride), alcohols and polyols (which may optionally also be substituted, etherified and/or esterified, such as butanol or glycol), ketones (such as acetone, methyl ethyl ketone, methyl isobutyl ketone cyclohexanone), esters (including fats and oils) and (poly)ethers, unsubstituted and substituted amines, amides (such as dimethylformamide),lactams (such as N-alkylpyrrolidones) and lactones, sulphones and sulphoxides (such as dimethyl sulphoxide). The carrier may also be a liquefied gaseous extender, i.e. liquid which is gaseous at standard temperature and under standard pressure, for example aerosol propellants such as halohydrocarbons, butane, propane, nitrogen and carbon dioxide.

The composition may further comprise one or more acceptable auxiliaries which are customary for formulating compositions (e.g. agrochemical compositions), such as one or more surfactants.

Examples of suitable surfactants include emulsifiers and/or foam formers, dispersants or wetting agents having ionic or nonionic properties, or mixtures thereof. Examples thereof are salts of polyacrylic acid, salts of lignosulphonic acid, salts of phenolsulphonic acid or naphthalenesulphonic acid, polycondensates of ethylene and/or propylene oxide with fatty alcohols, fatty acids or fatty amines (polyoxyethylene fatty acid esters, polyoxyethylene fatty alcohol ethers, for example alkylaryl polyglycol ethers), substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. A surfactant is typically used when the active ingredient and/or the carrier is insoluble in water and the application is made with water. Then, the amount of surfactants typically ranges from 5 to 40% by weight of the composition.

Further examples of auxiliaries which are customary for formulating agrochemical compositions include water repellent, siccatives, binder (adhesive, tackifier, fixing agent, such as carboxymethylcellulose, natural and synthetic polymers in the form of powders, granules or latices, such as gum arabic, polyvinyl alcohol and polyvinyl acetate, natural phospholipids such as cephalins and lecithins and synthetic phospholipids, polyvinylpyrrolidone, polyvinyl acetate, polyvinyl alcohol and tylose), thickeners, stabilizers (e.g. cold stabilizers, preservatives, antioxidants, light stabilizers, or other agents which improve chemical and/or physical stability), dyes or pigments (such as inorganic pigments, e.g. iron oxide, titanium oxide and Prussian Blue; organic dyes, e.g. alizarin, azo and metal phthalocyanine dyes), antifoams (e.g. silicone antifoams and magnesium stearate), preservatives (e.g. dichlorophene and benzyl alcohol hemiformal), secondary thickeners (cellulose derivatives, acrylic acid derivatives, xanthan, modified clays and finely divided silica), stickers, gibberellins and processing auxiliaries, mineral and vegetable oils, perfumes, waxes and nutrients (including trace nutrients, such as salts of iron, manganese, boron, copper, cobalt, molybdenum and zinc), protective colloids, thixotropic substances, penetrants, sequestering agents and complex formers. The choice of the carriers and/or auxiliaries will depend on the intended mode of application of the composition and/or on the physical properties of the active ingredient(s).

As previously mentioned, plants are known to use the RNA silencing pathway to fend off invading viruses. In mammals, until the recent findings of Y. Li et al. and P. V. Maillard et al. (Y. Li et al., Science, 342: 231-234, 2013; P. V. Maillard et al., Science, 342: 235-238, 2013), scientists could only evidence the gene-regulatory role of RNAi. Now, Y. Li et al. and P. V. Maillard et al. have evidenced that RNAi also acts as an antiviral response in mammals. Hence, the compounds of formula (I) can be used for stimulating the natural defense mechanism of mammals against viruses, in particular for stimulating the RNA-silencing-based defense mechanism of mammals against viruses.

Therefore, the present invention also relates to compounds of formula (I) as disclosed herein for use as a medicament, in particular for use in the treatment or prevention of a viral infection. The compound of formula (I) as disclosed herein may be used in a method for treating or preventing a viral infection in mammals which comprises administrating to a mammal in need thereof an effective amount of a compound of formula (I) as disclosed herein. The term "mammals" as used herein includes humans.

The present invention is explained in greater detail with the aid of the examples which follow.

EXAMPLES

Example 1: Identification of Modulators of Plant's Silencing Machinery—Use of SUC-SUL Reporter Plants The plants' RNA silencing pathway can be easily monitored with the artificially-created reporter plants called the "SUC-SUL *Arabidopsis* reporter plants" (Dunoyer et al., Nat. Genet. 37, 1356-1360, 2005).

The SUC-SUL *Arabidopsis* reporter plants are transgenic plants expressing an inverted-repeat (IR) double-stranded RNA designed to target the SULPHUR (SUL) transcript in the vasculature under the control of the SUC2 promoter (Truernit et al., Planta 196(3), 564-570, 1995). Once expressed, the dsRNA is processed into small interfering RNAs directing non-cell autonomous post-transcriptional gene silencing of the SULPHUR transcript, in turn causing vein-centered chlorosis. Since the observed chlorosis results from the silencing of the SULPHUR transcript, an expansion of the chlorosis, observable directly on the plants, is correlated with an intensification of the RNA silencing pathway at the molecular level.

Five days post-germination *A. thaliana* seedlings were sprayed with different solutions containing 300 ppm of an active molecule according to the invention, with dimethylsulfoxide (DMSO) 5% and a standard emulsifiable concentrate (EC) premix formulation (6 seedlings/test). Four repetitions were performed for each molecule. Control plants were treated with DMSO only (mock treated plants). The effects of the treatments on the SUC-SUL reporter plants were assessed 14 days after treatment under trans-illumination and digitally recorded with a stereo-microscope by measuring the surface and intensity of the chlorotic zone (percentage of chlorosis). Two independent experiments were carried out in order to estimate the average percentage of chlorosis for each molecule.

Results are shown in FIG. 4. Treatment with 300 ppm of Isoxazolone and analogues thereof led to a significant increase in the percentage of chlorosis confirming the activity of the active substance as putative robust enhancers of RNA silencing.

In order to discard molecules acting straightly on the promoter and not on the RNA silencing machinery, the active substances identified for their ability to increase the surface and intensity of the chlorotic zone were then tested, in a second step, on some AtSUC2-GFP reporter plants, which are specifically reporting the activity of the SUC2 promoter (Wright et al., Plant Physiol. 131, 1555-1565, 2003).

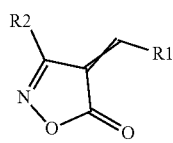

Example 2: Confirmation of the Molecular Effect of the Silencing Modulators

The enhancing effect of Isoxazolone on the RNAi machinery has been validated at the phenotypic and molecular levels. Four-week-old SUC-SUL *Arabidopsis* plants at rosette stage were sprayed with Isoxazolone at 200 ppm. Seven days after treatment, it was shown that Isoxazolone induced a clear expansion of the RNAi-dependent vein-centered chlorotic phenotype, which was not observed with DMSO only (mock control).

The plant aerial tissues were collected and analyzed molecularly using state-of-the-art methodologies. The visual expansion of the chlorosis correlated with reductions in SUL transcript levels, as analyzed by real-time qRT-PCR (FIG. 1), as well as reductions in SUL protein levels quantifiable on Western blot analyses. Furthermore, these effects were associated with an over-accumulation of both SUL 21-nt and 24-nt long siRNAs derived from the transgenic SUL. Altogether, these data support that Isoxazolone induces the plant's RNAi pathway.

Example 3: Antiviral Efficacy of Silencing Modulators on *Arabidopsis*

The Turnip mosaic virus (TuMV) belongs to the Potyviridae, the largest family of known plant viruses. This virus infects a wide range of plants, in particular Brassicaceae. TuMV genome consists of a positive-sense single-stranded RNA molecule (+ssRNA). The antiviral efficacy of Isoxazolone was tested with a fluorescently-tagged potyvirus (TuMV-GFP) in order to specifically pinpoint when and where the effect of the molecules is induced during virus primary infection, as well as its local or systemic spread.

*Arabidopsis* plants were sprayed with 100 or 200 ppm of Isoxazolone 3 days before infecting the plants with the TuMV-GFP virus. Virus titers were measured by qPCR and/or virus protein accumulation on Western blot analyses and by counting the number of primary infection foci under UV light in the case of the TuMV-GFP.

Figure 2:
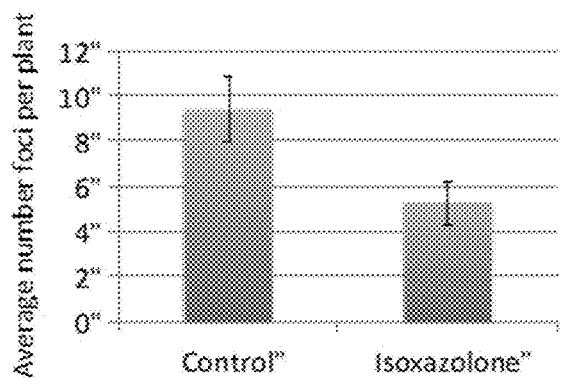
FIG. 2 represents the average number of infection foci at five days post-infection on inoculated leaves. Error bars represent standard deviation from twelve plants.

Isoxazolone leads to a clear reduction of the accumulation of virus titers five days-post-infection on the *Arabidopsis* plants. A strong reduction of virus accumulation was consistently observed with TuMV-GFP both on inoculated leaves (FIG. 2) and on systemic tissues upon treatment with Isoxazolone, as measured by the reduction of the accumulation of the TuMV-derived HcPro mRNA levels (FIG. 3).

The invention claimed is:

1. A method for controlling viral disease in plants, comprising applying to the plants at least one compound of formula (I):

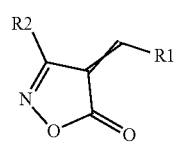

(I)

wherein
R1 is a thienyl or phenyl, wherein said thienyl or phenyl may be substituted with one or more substituents independently selected from the group consisting of halogen, $(C_1-C_6)$alkyl, $(C_1-C_6)$alkylthio, $((C_1-C_6)$alkoxy$)(C_1-C_6)$alkyl, $((C_1-C_6)$alkylthio$)(C_1-C_6)$alkyl and phenyl; and
R2 is a phenyl which may be substituted with one or more substituents independently selected from the group consisting of halogen, $(C_1-C_6)$alkyl and $(C_1-C_6)$alkoxy.

2. The method according to claim 1, wherein R1 is selected from the group consisting of 2-thienyl, phenyl, 3-methyl-2-thienyl, 5-methyl-2-thienyl, 2-methylphenyl, 4-methylphenyl, 4-phenyl-2-thienyl, 5-phenyl-2-thienyl, 4-bromo-2-thienyl, 5-bromo-2-thienyl, 5-chloro-2-thienyl, 4-bromo-5-methyl-2-thienyl, 4-bromo-5-ethyl-2-thienyl, 3-(methyl sulfanyl)-2-thienyl, 4-bromo-5-[(methylsulfanyl)methyl]-2-thienyl, 3-(methoxymethyl)-2-thienyl, 2,6-dimethylphenyl, 2,4,5-trimethylphenyl, 2,4,6-trimethylphenyl and 2,6-dichlorophenyl.

3. The method according to claim 1, wherein R2 is selected from the group consisting of phenyl, 2-chlorophenyl, 2-fluorophenyl, 3-chlorophenyl, 4-fluorophenyl, 2,3-dichlorophenyl, 2,4-dichlorophenyl, 2,5-dichlorophenyl, 3,4-dichlorophenyl, 2-chloro-5-fluorophenyl, 2-methylphenyl, 4-methylphenyl, 2-methoxyphenyl, 3-methoxyphenyl and 4-methoxyphenyl.

4. The method according to claim 1, wherein the control is based on a stimulation of the natural defense mechanism of plants against viruses.

5. The method according to claim 4, wherein the natural defense mechanism of plants against viruses is a RNA-silencing based plant defense mechanism.

6. The method according to claim 1, wherein said method is a preventive method.

7. The method according to claim 1, wherein said plants are selected from the group consisting of cotton, flax, grapevine, fruit, vegetables, crop plants, ornamental plants for gardens and wooded area and genetically modified varieties of each of these plants.

8. The method according to claim 1, wherein said plants are selected from the group consisting of *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp., *Rubiaceae* sp., *Theaceae* sp., *Sterculiceae* sp., *Rutaceae* sp.; *Solanaceae* sp., *Liliaceae* sp., *Asteraceae* sp., *Umbelliferae* sp., *Cruciferae* sp., *Chenopodiaceae* sp., *Cucurbitaceae* sp., *Alliaceae* sp., *Papilionaceae* sp., *Asteraceae* sp., *Brassicaceae* sp., *Fabacae* sp., *Papilionaceae* sp., *Solanaceae* sp. and *Chenopodiaceae* sp.

9. The method according to claim 1, wherein said viruses are selected from the group consisting of the following families or genus: *Caulimoviridae, Geminiviridae, Bromoviridae, Closteroviridae, Comoviridae Potyviridae, Sequiviridae, Tombusviridae, Rhabdoviridae, Bunyaviridae, Partitiviridae, Rheoviridae, Capillovirus, Carlavirus, Enamovirus, Furovirus, Hordeivirus, Idaeovirus, Luteovirus, Marafivirus, Potexvirus, Sobemovirus, Tenuivirus, Tobamovirus, Tobravirus, Trichovirus, Tymovirus* and *Umbravirus*.

10. The method according to claim 1, wherein said viruses are selected from the group consisting of Turnip mosaic virus, turnip crinkle virus, bean pod mottle virus, cauliflower mosaic virus, tobacco mosaic virus, tomato bushy stunt virus, rice ragged stunt virus, cucumber mosaic virus, barley yellow dwarf virus, beet yellows virus, lettuce yellows virus, maise mosaic virus, peanut stunt virus and potato virus Y.

11. The method according to claim 1, wherein the compound of formula (I) is applied by spraying to the plants.

12. The method according to claim 1, wherein the compound of formula (I) is applied to the plants in an amount ranging from 0.01 to 5 kg/ha.

13. The method according to claim 1, wherein R1 is selected from the group consisting of 2-methylphenyl, 4-methylphenyl, 2,6-dimethylphenyl, 2,4,5-trimethylphenyl, 2,4,6-trimethylphenyl and 2,6-dichlorophenyl.

14. The method according to claim 13, wherein R2 is 2-chlorophenyl.

* * * * *